(12) United States Patent
Reimann et al.

(10) Patent No.: US 7,951,980 B2
(45) Date of Patent: May 31, 2011

(54) PROCESS AND APPARATUS FOR THE RECOVERY OF ETHYLENE GLYCOL IN THE PRODUCTION OF POLYETHYLENE TEREPHTHALATE

(75) Inventors: Randolf Reimann, Alzenau (DE); Rolf Ambrassat, Frankfurt am Main (DE)

(73) Assignee: Lurgi Zimmer GmbH, Frankfurt am Main (DE)

( * ) Notice: Subject to any disclaimer, the term of this patent is extended or adjusted under 35 U.S.C. 154(b) by 0 days.

(21) Appl. No.: 12/535,732

(22) Filed: Aug. 5, 2009

(65) Prior Publication Data

US 2010/0041925 A1  Feb. 18, 2010

(30) Foreign Application Priority Data

Aug. 18, 2008 (DE) .................. 10 2008 044 440

(51) Int. Cl.
 C07C 27/26 (2006.01)
 C07C 27/28 (2006.01)
(52) U.S. Cl. ...... 568/871; 568/868; 568/870; 528/308.1
(58) Field of Classification Search .................. 568/870, 568/871
 See application file for complete search history.

(56) References Cited

U.S. PATENT DOCUMENTS

| | | | |
|---|---|---|---|
| 4,758,650 A | 7/1988 | Schulz Van Endert | |
| 5,294,305 A | 3/1994 | Craft, Jr. et al. | |
| 5,932,105 A | 8/1999 | Kelly | |
| 6,703,478 B2 | 3/2004 | Nakane | |
| 6,864,345 B2 | 3/2005 | Reimann | |
| 7,084,234 B2 | 8/2006 | Wilhelm et al. | |

FOREIGN PATENT DOCUMENTS

WO  WO 96/35654  5/1996

OTHER PUBLICATIONS

Chinese Patent Application 000001974508A, published Jun. 6, 2007 (abstract only).
Database WPI Week 197843, Thompson Scientific, London, GB, AN1978-77178A, XP002542695 & JP 53 106794 A, Mitsubishi Rayon Co., Ltd., published Sep. 18, 1978 (abstract only).

*Primary Examiner* — Brian J Davis
(74) *Attorney, Agent, or Firm* — Jonathan Myers; Andrew Wilford

(57) ABSTRACT

A method and apparatus are disclosed for the recovery of ethylene glycol in a polyethylene terephthalate (PET) production process, in which water accumulating in the esterification reaction is mixed with a process fluid containing 2-methyl-1,3-dioxolane (MDO). The mixing is carried out in a tank arranged upstream of a rectification column. Through the increase in the water content in the fluid, a shift in the reaction equilibrium takes place and consequently a cleavage of the 2-methyl-1,3-dioxolane present into ethylene glycol and acetaldehyde takes place. Following the cleavage reaction, the mixture is fed from the tank into a rectification column, whereby the ethylene glycol produced from the cleavage reaction is returned to the PET production process.

10 Claims, 1 Drawing Sheet

PROCESS AND APPARATUS FOR THE RECOVERY OF ETHYLENE GLYCOL IN THE PRODUCTION OF POLYETHYLENE TEREPHTHALATE

CROSS REFERENCE TO RELATED APPLICATIONS

This application claims the benefit of the priority of German Patent Application DE 10 2009 044 440.5 filed 18 Aug. 2008, the contents of which are expressly incorporated herein.

FIELD OF THE INVENTION

The present invention relates to a process and an apparatus for the recovery of ethylene glycol in the production of polyethylene terephthalate (PET). More particularly this invention concerns a process and apparatus for recovering ethylene glycol from spent ethylene glycol (SEG), which accumulates as a byproduct of the polycondensation reaction forming PET. The SEG contains 2-methyl-1,3-dioxolane (MDO), in which ethylene glycol is bonded in the form of an acetal.

BACKGROUND OF THE INVENTION

PET is produced via an esterification reaction of the carboxyl groups of terephthalic acid and the hydroxyl groups of ethylene glycol, wherein water separates. The process waste water accumulating through the esterification reaction, which in addition to acetaldehyde, i.a., contains considerable amounts of ethylene glycol, is subjected to a rectification (process column) for the purpose of the recovery of the ethylene glycol in the sump of the column. The ethylene glycol may then either be recovered or returned to the process for preparing PET. In order to keep the loss of ethylene glycol low, methods according to the prior art as a rule have structurally sophisticated rectification columns with a plurality of plates or packings. A relatively high reflux ratio is necessary for a satisfactory separation of the contaminants contained in the process waste water, which means a substantial power requirement. Despite the separation process that is expensive in terms of energy, the partially purified process wastewater obtained is usually subsequently guided over a stripper due to its residual content of acetaldehyde and other volatile organic components before it is fed to a water treatment plant. In the PET production process moreover substantial amounts of contaminated ethylene glycol (spent ethylene glycol, SEG) accumulates as a byproduct of the polycondensation reaction. The SEG comes primarily from the vacuum system and the ethylene glycol circuit of prepolycondensation and contains 2-methyl-1,3-dioxolane (MDO), in which ethylene glycol is bonded in the form of an acetal. The SEG process flows from the various process steps of the PET production process are subjected jointly with the process wastewater to a reprocessing in the rectification column (also referred to here as "process column" or "column") and then fed again to the PET production process. The MDO is a low-boiler, which cannot be held back in the process column, i.e., leaves the process column overhead. Most of the MDO is then condensed and reaches the process wastewater as a contaminant. A small part of the MDO is emitted via the exhaust air. The MDO is the actual reason for the relatively high losses of ethylene glycol in the process column of PET systems.

International patent application WO 96/35654 discloses a method in which the process wastewater from the PET production process after the process column (overhead product) is partially condensed and subsequently subjected to an inert gas stripping of a reverse osmosis. A reconcentration of the ethylene glycol remaining in the partially purified process wastewater is thereby carried out through the application of a pressure that is greater than the osmotic pressure of the reconcentrated solution. The water is thus pressed through the membrane against the tendency towards the osmotic concentration equilibrium. The permeate comprises pure water, which can be directly discharged so that a (complex) water treatment plant is no longer necessary. In addition, the method permits higher ethylene glycol concentrations in the overhead product of the process column, which on the one hand reduces the thermal energy required for the column and as a result reduces the coolant required for the subsequent condensation. Furthermore, the number of the column trays required can be reduced. The retentate (concentrate) from the reverse osmosis is returned to the process, wherein a recirculation is provided either into the reactor or directly into the process column. Through this method, although the recovery of ethylene glycol by means of reverse osmosis is improved compared to conventional methods, the problem of the loss of ethylene glycol in the form of MDO is neither recognized nor solved.

OBJECTS OF THE INVENTION

An object of the present invention is now to provide a process and an apparatus, which are suitable for the recovery of ethylene glycol in the production of PET.

A further object of the invention is to render possible a saving of investment and/or operating costs and at the same time to implement the recovery of ethylene glycol from SEG in an environmentally friendly manner.

A further object of the invention is to provide a simple, functional apparatus for ethylene glycol recovery, requiring a low system expenditure and providing energy savings, in particular, by providing a reduction in the consumption of raw material with a minimal expenditure and by optimizing the ethylene glycol recovery.

Further objects and advantages of the present invention are shown by the following statements.

SUMMARY OF THE INVENTION

According to the invention, the object is attained through a process for recovering ethylene glycol in the PET production process, wherein the PET production process contains an esterification reaction in which process wastewater is produced, wherein the process waste water is subjected to at least one separation step preferably a rectification, in which at least a part of the contaminants present in the process wastewater are separated and thus a partially purified process waste water is produced, wherein at least a part of the partially purified process wastewater is mixed with a fluid containing 2-methyl-1,3-dioxolane (MDO) preferably one or more spent ethylene glycol (SEG) process flows in a container arranged upstream of the rectification column, and the MDO present in the mixture produced is cleaved completely or partially into ethylene glycol and acetaldehyde.

In the PET production process during the esterification or condensation reaction of the terephthalic acid with ethylene glycol (process) water is produced which leaves the esterification and condensation reactors together with other substances as exhaust vapor. The cited substances (referred to below as a whole as contaminants) are, i.a., ethylene glycol, acetic acid and acetaldehyde. They must be recovered for reasons of economy or removed to comply with environmental regulations. The process waste water, that is the sum of (process) water and contaminants, is therefore subjected to one or more separation steps, wherein a first separation usually takes place by distillation in a rectification column. There most of the ethylene glycol present is separated, remaining in the sump, and which may then be either recovered or returned to the PET process, and the overhead product of the column is subsequently fed to a condenser, wherein a part of the acetaldehyde and other low-boilers remain in the gas phase and are fed as exhaust air to a thermal or catalytic combustion. Through a first separation step of this type a partially purified process waste water is produced, which according to previous practice is often also guided over a stripper before it is fed into a water treatment plant or is directly ejected as waste water.

In addition to partially purified process waste water, substantial quantities of contaminated ethylene glycol (spent ethylene glycol, SEG) accumulate in the PET production process, which contains, i.a., MDO. The SEG comes in particular from the vacuum system and the ethylene glycol circuit of the prepolycondensation. The SEG process flows from the various process steps of the PET production process are often combined in a collecting tank (SEG tank or SEG collecting tank), subsequently subjected to a separation step in a rectification column and then returned to the PET production process.

The MDO is a low-boiler which cannot be held back in the rectification column, i.e., leaves the column overhead together with the (process) water. The large part of the MDO is then condensed together with the (process) water and discharged as part of the partially purified process wastewater. A small part of the MDO is emitted via the exhaust air. The existence of the MDO is the actual cause of the relatively high losses of EG in the column of PET systems. MDO is stable under neutral; and slightly alkaline pH conditions, in the acid range depending on the water content, preferably at a pH of 3 to 6, MDO decomposes into the starting materials ethylene glycol and acetaldehyde. The formation as well as cleavage of the MDO are acid-catalyzed.

It was recognized that the partially purified process waste water (or a part thereof) can be used to increase the water content in ethylene glycol (SEG) contaminated with MDO from the PET production process to the extent that by shifting the chemical equilibrium a cleavage of a substantial part of the MDO present into ethylene glycol and acetaldehyde takes place. An acceleration of the MDO cleavage is rendered possible by feeding acid components in the partially purified process wastewater. Nevertheless, a certain dwell time for the course of the MDO cleavage reaction is necessary. For this reason the partially purified process wastewater and the spent glycol are combined in a tank from which the rectification column is then fed. The tank provides the necessary dwell time for the cleavage reaction. Compared to a rectification process, which does not provide an upstream MDO cleavage, this thus has the advantage that the reflux ratio in the process column can be reduced due to the lower MDO content of the exhaust vapor, which is advantageous for economic reasons. Acetaldehyde is formed as a further reaction product from the MDO cleavage. This is a low-boiler that can be fed via process column partially via the gas phase to an exhaust air treatment.

In the present application, a partially purified process wastewater means process waste water that has passed through at least one separation step. A reprocessing by distillation in a column is provided as a preferred first separation step, wherein the forming partially purified process wastewater preferably contains the substances listed in table 1 in the quantities given. As the table shows, the partially purified process wastewater also has a significant MDO content.

All of the percentages given here are to be understood as percent by weight unless stated otherwise. The basis is the respectively cited mass flow.

The term "process" or "PET production process" or "PET production method" means the entire process for producing PET, including all conversions and substance flows. Accordingly, "system" means the entire system for producing PET.

Expressions such as "water with:" or "ethylene glycol with:" refer to the main component of the respective material flow, that is, the residual amount after removal of the contaminants. Preferably these have a content of the main component of at least 30% by weight, wherein at least 60% by weight and in particular 90% by weight are particularly preferred.

The terms "water," "(process) water" or "process wastewater" do not reveal anything about the state of aggregation. The partially purified process wastewater can consequently be present not only in liquid form, but also in gaseous form.

TABLE 1

Partially purified process wastewater after process column and condenser

| | |
|---|---|
| Mass Flow (total) | 185-195 kg/t PET |
| Water with: | |
| Ethylene glycol | 0.4-0.6% |
| 2-methyl-1,3 dioxolane | 0.3-0.6% |
| Acetic Acid | 0.1-0.2%*) |
| | 0.01-0.02%**) |
| 1,4-dioxane | 0.04-0.06% |
| Acetaldehyde | 0.9-1.5% |
| Temperature | 30-40° C. |

*)With the use of antimony acetate as catalyst in the PET production process.
**)With the use of antimony trioxide as catalyst in the PET production process It can be advantageous to subject the partially purified process wastewater to one or more further separation steps before the mixing with SEG, wherein this is preferably a (further) process column and/or a stripper. Stripped, partially purified process wastewater preferably contains the substances listed in Table 2 in the specified amounts.

TABLE 2

Partially purified process wastewater after process column and stripper

| | |
|---|---|
| Mass Flow (total) | 170-180 kg/t PET |
| Water with: | |
| Ethylene glycol | 0.2-0.6% |
| 2-methyl-1,3 dioxolane | 0.01-0.05% |
| Acetic Acid | 0.06-0.2%*) |
| | 0.006-0.02%**) |
| 1,4-dioxane | 0.01-0.05% |
| Acetaldehyde | 0.01-0.03% |
| Temperature | 30-60° C. |

*)With the use of antimony acetate as catalyst in the PET production process.
**)With the use of antimony trioxide as catalyst in the PET production process The stripping is preferably carried out thereby with air as strip gas.

The above-referenced method according to the invention is particularly advantageous if at least a part of the partially purified process wastewater is subjected to at least one reverse osmosis and/or ultra/nanofiltration before the mixing with the fluid containing MDO wherein preferably that part of the process wastewater which accumulates with the reverse osmosis and/or ultra/nanofiltration as retentate is used at least in part for mixing with the fluid containing 2-methyl-1,3- dioxolane. Various advantages result from a process control of this type. Depending on the embodiment (single-stage to three-stage), the use of a reverse osmosis makes it possible to omit a (complex) wastewater treatment, since the permeate comprises slightly contaminated to uncontaminated water. According to the invention, however, even with the use of reverse osmosis and/or ultra/nanofiltration depending on the embodiment of the membrane methods and the valid environmental regulations a final wastewater treatment can nevertheless be provided, wherein, however, this can be embodied more simply and operated at less expense due to the pre-treatment of the process wastewater (here: permeate). In addition, the use of a reverse osmosis leads to lower MDO concentrations in the overhead product of the rectification column, which reduces the thermal energy needed for the column (reflux) and consequently the coolant requirement for the subsequent condensation. Furthermore, the number of column trays needed can be reduced.

In addition to the referenced advantages, through the method according to the invention, i.e., through the cleavage of the MDO, furthermore ethylene glycol can be recovered. The retentate (concentrate) from the reverse osmosis, i.e., the part of the partially purified process wastewater enriched with ethylene glycol, is thereby preferably used to increase the water content in the SEG. Although the (process) water returned to the PET production process, preferably into the column, must be evaporated and subsequently condensed, in contrast to the method according to the prior art this disadvantage in terms of energy is more than compensated for by the recovered ethylene glycol. In contrast to the prior art, therefore, no minimization of the retentate volume by means of reverse osmosis needs to be undertaken. The method according to the invention therefore makes it possible to keep the pressure—and thus the energy expenditure—lower during the reverse osmosis. Furthermore, a part of the fed (process) water is used during the cleavage of the MDO. The reverse osmosis and/or ultra/nanofiltration is preferably carried out at temperatures of 20-50° C. and/or pressures of 5-70 bar (g).

Partially purified, in particular not stripped process wastewater contains significant quantities of 1,4 dioxane (see Tables 1 and 2). Since 1,4 dioxane is virtually not biologically degradable, the frequently required low outflow values after water treatment plant with respect to chemical cumulative parameters such as, e.g., COD (chemical oxygen demand) and total organic carbon (TOC) are not achieved. With the described application of reverse osmosis and/or ultra/nanofiltration, a large part of the 1,4 dioxane contained in the process wastewater is returned to the PET production process and from there is easily treated via the exhaust gas in a thermal or catalytic exhaust air purification. The permeate depleted from 1,4 dioxane is fed to a water treatment plant, wherein with the identical equipment of the water treatment plant a clearly improved outflow quality can now be achieved with respect to chemical cumulative parameters such as e.g. COD and TOC.

After running through the reverse osmosis and/or ultra/nanofiltration, the partially purified process wastewater preferably contains the substances listed in Table 3 (retentate) and Table 4 (permeate) in the amounts listed

TABLE 3

Partially purified process wastewater/retentate from reverse osmosis.

| Method with stripper: | |
| --- | --- |
| Mass Flow (total) | 4-22 kg/t PET |
| Water with: | |
| Ethylene glycol | 3-10% |
| 2-methyl-1,3 dioxolane | 0.1-0.6% |
| Acetic Acid | 0.5-2%*) |
|  | 0.05-0.2%**) |
| 1,4-dioxane | 0.1-0.6% |
| Acetaldehyde | Not relevant |
| Temperature | 20-40° C. |
| Method without stripper: | |
| Mass Flow (total) | 4-22 kg/t PET |
| Water with: | |
| Ethylene glycol | 3-10% |
| 2-methyl-1,3 dioxolane | 3-10% |
| Acetic Acid | 0.7-2%*) |
|  | 0.07-0.2%**) |
| 1,4-dioxane | 0.5-0.8% |
| Acetaldehyde | Not relevant |
| Temperature | 20-40° C. |

*)With the use of antimony acetate as catalyst in the PET production process.
**)With the use of antimony trioxide as catalyst in the PET production process

TABLE 4

Partially purified process wastewater/permeate from reverse osmosis.

| Method with stripper: | |
| --- | --- |
| Mass Flow (total) | 152-170 kg/t PET |
| Water with: | |
| Ethylene glycol | 0.05-0.15% |
| 2-methyl-1,3 dioxolane | ca. 0.005% |
| Acetic Acid | 0.05-0.1%*) |
|  | 0.005-0.01%**) |
| 1,4-dioxane | 0.002-0.006% |
| Acetaldehyde | Not relevant |
| Temperature | 20-40° C. |
| Method without stripper: | |
| Mass Flow (total) | 168-185.7 kg/t PET |
| Water with: | |
| Ethylene glycol | 0.05-0.15% |
| 2-methyl-1,3 dioxolane | ca. 0.07% |
| Acetic Acid | 0.07-0.12%*) |
|  | 0.007-0.012%**) |
| 1,4-dioxane | 0.002-0.006% |
| Acetaldehyde | Not relevant |
| Temperature | 20-40° C. |

Discharge as wastewater for final cleaning in a chemical/biological waste water cleaning.
*)With the use of antimony acetate as catalyst in the PET production process.
**)With the use of antimony trioxide as catalyst in the PET production process With the use of a reverse osmosis, the retention degrees listed in Table 5 below are to be anticipated:

TABLE 5

Retention degrees* of reverse osmosis.

| | |
|---|---|
| Ethylene glycol | 75-85% |
| 2-methyl-1,3 dioxolane | 80-90% |
| Acetic Acid | 45-55% |
| 1,4-dioxane | 85-95% |
| Acetaldehyde | Not relevant |

*Method with/without stripper.

In the present application, SEG process flows are to be understood to mean all process flows contaminated with MDO in the PET production process, which essentially contain ethylene glycol. The SEG or the SEG process flows used in the method according to the invention preferably have an ethylene glycol content of at least 30% by weight, wherein a content of at least 60% by weight and in particular at least 90% by weight is particularly preferred. The SEG process flows used according to the invention are preferably the material flows which the ethylene glycol circuit of the prepolycondensation comprises, as well as SEG process flows from the vacuum system of the prepolycondensation.

The SEG from the prepolycondensation preferably contains the substances listed in Table 6 in the amounts given.

TABLE 6

SEG flow ***from prepolycondensation into SEG collecting tank

| | |
|---|---|
| Mass flow (total) | 90-110 kg/t |
| Ethylene glycol with: | |
| Water | 3-7% |
| 2-methyl-1,3 dioxolane | 0.2-0.7% |
| Acetic Acid | ca. 0.1%*) |
| | ca. 0.01%**) |
| 1,4-dioxane | 0.02-0.04% |
| Acetaldehyde | Not relevant |
| Temperature | 35-60° C. |

*)With the use of antimony acetate as catalyst in the PET production process
**)With the use of antimony trioxide as catalyst in the PET production process
***Method with/without stripper.

Since the SEG or the SEG process flows are mostly present in liquid form and the process wastewater for treatment in the reverse osmosis unit likewise has to be available in liquid form, it is preferred to mix SEG and partially purified process wastewater in liquid form. However, a mixing is also conceivable in which the SEG as well as the partially purified process wastewater are present in gaseous form, or a mixing in which one of the components to be mixed is available entirely or partially in gaseous form, while the other is entirely or partially liquid.

According to the present invention, before or during the mixing of the SEG with the partially purified process wastewater preferably a combination of two or more of the SEG process flows of the PET production process is provided. An SEG collecting tank such as is already available in most systems according to the prior art is preferably used in the combination of the SEG process flows. In addition, one or more further tanks can be provided in which the mixing of the SEG with the partially purified process wastewater and the conversion of the MDO take place. However, it is preferred according to the invention that the mixing likewise takes place in the SEG collecting tank, which to that end i.a. is supplemented with one or more feed lines for partially purified process wastewater. In this manner an additional container for the conversion of the MDO is not needed, which reduces the number of system parts necessary, with which a reduction of the investment and operating expenditure is achieved. Moreover, mixing elements can be provided which, for example, are located either in the tank itself or are arranged as static mixing elements upstream of the tank. Accordingly, instead of separate feed lines for SEG and partially purified process wastewater, the container can also have one or more feed lines that supply SEG and partially purified process wastewater jointly. The (one or more) tank(s) is preferably designed such that at least 20% by weight, preferably at least 40% by weight of the MDO present in the supplied SEG and/or the MDO present in the supplied in the partially purified process wastewater can be cleaved into ethylene glycol and acetaldehyde. Accordingly, a cited method for the recovery of ethylene glycol is particularly preferred when in the (one or more) tank(s) 20-80% by weight, preferably 30-70% by weight, particularly preferably 40-60% by weight of the MDO present in the supplied SEG and/or in the supplied partially purified process water is cleaved into ethylene glycol and acetaldehyde or the MDO cleavage rate in the tank achieves these values.

In addition to the above referenced method, the present invention also includes a system for the production of PET with one or more esterification and/or transesterification reactors as well as one or more devices for the production of a partially purified process wastewater through the separation of contaminants present in the process wastewater, which preferably is a rectification column, wherein the system has one or more tanks, which have at least one feed line for partially purified process wastewater and at least one feed line for a fluid containing MDO (preferably an ethylene glycol process flow) and/or one or more feed lines for a mixture of partially purified process wastewater and a fluid containing MDO.

A cited system is to be considered particularly advantageous when it has a reverse osmosis device and/or an ultra/nanofiltration device, which is arranged upstream of the tank in terms of process engineering.

In this case, the system preferably has one or more lines that feeds that part of the partially purified process wastewater which accumulates as retentate in the reverse osmosis unit and/or ultra/nanofiltration unit (or a part thereof) directly or indirectly to the tank. The system therefore advantageously has one or more lines that run between the reverse osmosis unit and/or the ultra/nanofiltration unit and the tank.

The inflow of partially purified process wastewater into the tank is preferably controlled depending on the water content of the mixture in the tank, which is preferably measured periodically. If a reverse osmosis unit and/or an ultra/nanofiltration unit is provided, the pressure in the reverse osmosis unit and/or ultra/nanofiltration unit or the degree of the reconcentration can also be controlled depending on the water content in the tank in order to achieve an increased or lower enrichment of ethylene glycol and/or acetic acid or a higher or lower water content. It can also be advantageous to control the separation power of the process column depending on the water content in the tank, for example, via the adjustment of the reflux ratio.

A system such as is described above is particularly advantageous when the volume of the container is dimensioned such that the dwell time is 0.2-4 hours, preferably 0.5-3 hours, particularly preferably 1-2 hours.

In this manner a decomposition of a substantial part of the MDO is ensured. The tank serves at the same time as a buffer for SEG and/or partially purified process wastewater. "Dwell time" means the dwell time of the contents of the tank, i.e., the mixture of partially purified process wastewater and SEG.

According to a further preferred embodiment, in the above-mentioned method or in the cited system the cleavage of the MDO takes place in the presence of one or more catalysts, wherein the catalysts are preferably one or more of the following: "organic aliphatic and aromatic acids, preferably acetic acid."

A referenced method is in particular advantageous when one or more acids contained in the process wastewater, preferably acetic acid are reconcentrated (preferably by means of reverse osmosis) and used as catalysts for the cleavage of the MDO.

This is another reason why the use of a reverse osmosis and/or ultra/nanofiltration is favored with the method according to the invention. Through reverse osmosis and/or ultra/nanofiltration not only can a reconcentration of MDO in the process wastewater and a recovery of ethylene glycol be achieved, but also a reconcentration of other contaminants or ingredients, in particular organic acids such as acetic acid. These are thus kept in the process and can be used, for example, as catalysts in the MDO cleavage. If the amount of catalysts is too small, an addition from outside is also conceivable. Preferably the catalysts are substances that essentially do not negatively affect the other processes connected with PET production and thus can be guided in the circuit. That means that the catalysts, which are preferably acid compounds, can be returned to the tank via the partially purified process wastewater and/or the SEG process flows and thus can accelerate the MDO cleavage.

The cleavage of the MDO is an equilibrium reaction. Consequently, with the increase of the water concentration in the mixture, the chemical equilibrium is shifted in the direction of the MDO cleavage products ethylene glycol and acetaldehyde. Since the water in the process column must be evaporated again, it is advantageous to keep the water proportion in the mixture low. The conversion of the MDO in the tank therefore preferably occurs under conditions such as are listed in Table 7. Thus on the one hand a cleavage of an essential part of the MDO is ensured and on the other hand the additional expenditure in connection with a return of the water into the process is thus allowed for.

TABLE 7

Conditions for MDO cleavage in the SEG collecting tank* dwell time: 0.5-3 h, preferably: 1-2 h
temperature: 35-95° C., preferably: 40-60° C.
concentration of water: ≧10%, preferably: 15-25%
concentration of acid 0.1-1%, preferably: 0.2-0.4%
exhaust air Discharge suction of the acetaldehyde formed, Discharge
via exhaust air collector line for thermal or catalytic exhaust air treatment
cleavage rate of MDO: 20-80-%, preferably: 40 to 60%

*Method with/without stripper

As also set forth in Table 7, another possibility for shifting the equilibrium in the direction of the MDO is to suction off acetaldehyde from the tank. The pressure in the container is thus preferably adjusted such and optionally coordinated with the other conditions (cf. Table 7) such that the cleavage rate cited in Table 7 is achieved.

The quantity of recovered ethylene glycol is shown in Table 8.

TABLE 8

Ethylene glycol recovery rate
With the use of a process column and a stripper:
General recovery rate of ethylene glycol:

| | |
|---|---|
| through reverse osmosis (RO) | 0.3-0.9 kg/t PET |
| through MDO cleavage | 0.1-0.5 kg/t PET |

The following ethylene glycol recovery rates apply for stripped partially purified process wastewater.

| | |
|---|---|
| RO + MDO cleavage: | 0.5-1.3 kg/t PET |

Through adjustment of the operating parameters of the existing stripper system to the reverse osmosis/MDO cleavage, the EG recovery rate can be increased to at least 1.5 kg/t
With the use of a process column, without the use of a stripper:
General recovery rates of ethylene glycol:

| | |
|---|---|
| through RO | 0.6-1.0 kg/t PET |
| through MDO cleavage | 0.1 to 1.0 kg/t PET |

The following ethylene glycol recovery rates apply for unstripped partially purified process wastewater:

| | |
|---|---|
| RO + MDO cleavage | 0.8-1.8 kg/t PET |

An above-referenced method is particularly important when the mixture of SEG and partially purified process wastewater has a water content of at least 10% by weight, preferably 13 to 45% by weight, particularly preferably 15-25% by weight. Preferably the inflow of SEG and partially purified process wastewater to the tank is controlled such that the above-referenced water content of the mixture is achieved.

If an MDO cleavage rate of approximately 50% is provided, the mixture of SEG and partially purified process wastewater preferably contains the substances listed in Table 9 in the listed quantities. This is preferably the process flow that is guided back into the PET production process.

TABLE 9

Mixture SEG flow + partially purified process wastewater (retentate) after MDO cleavage at 50%.

| Method with stripper: | |
|---|---|
| Mass Flow (total) | 94-132 kg/t PET |
| Ethylene glycol with: | |
| Water | 10-20% |
| 2-methyl-1,3 dioxolane | 0.2-0.7% |
| Acetic Acid | 0.1-0.3%*) |
| | 0.01-0.03%**) |
| 1,4-dioxane | 0.05-0.08% |
| Acetaldehyde | Not relevant |
| Temperature | 35-60° C. |
| Method without stripper: | |
| Mass Flow (total) | 94-132 kg/t PET |
| Ethylene glycol with: | |
| Water | 10-20% |
| 2-methyl-1,3 dioxolane | 0.3-0.8% |
| Acetic Acid | 0.2-0.4%*) |
| | 0.02-0.04%**) |
| 1,4-dioxane | 0.08-0.12% |
| Acetaldehyde | Not relevant |
| Temperature | 35-60° C. |

*)With the use of antimony acetate as catalyst in the PET production process.
**)With the use of antimony trioxide as catalyst in the PET production process As mentioned, the return of the partially purified process wastewater into the PET production process is carried out in the form of a mixing with the SEG. In this respect an above-referenced method is particularly advantageous when the mixture (completely or in part) after the cleavage of at least part of the MDO is returned to the PET production process at one more points. It is particularly preferred thereby to provide a return to a process column of the PET polycondensation system and/or an ethylene glycol recovery system.

The material flows referenced in the application are mutually interdependent and the decision on how their composition and other properties are to be selected depends on the objective that is to be achieved. It was established that material flows that lie in the concentration ranges with respect to their composition as they are given in the tables above are preferred. These ensure an MDO conversion rate that is particularly advantageous with respect to ethylene glycol formation and for economic reasons. However, the invention is not restricted to the given values.

DETAILED DESCRIPTION OF THE DRAWING

Figure 1:
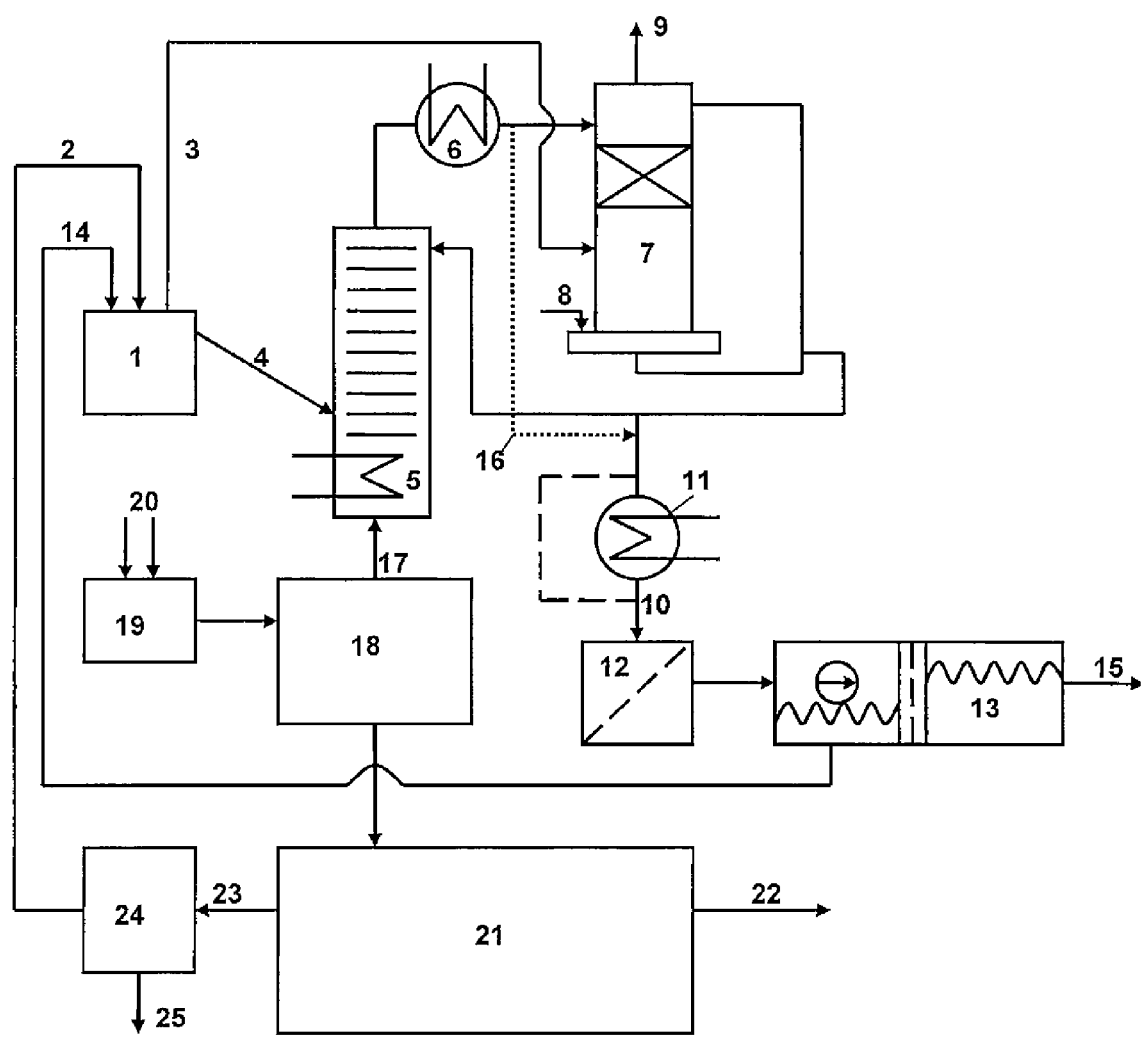
FIG. 1 is a flow diagram, which illustrates the process steps, both with and without a stripper, which is optional, the elements of the apparatus parts and the material flows that are relevant or preferred for the ethylene glycol recovery in the PET production process.

In the PET production process during the esterification or condensation reaction of the terephthalic acid with ethylene glycol (process) water is produced which leaves the esterification reactor 18 together with other substances as exhaust vapor which exits the esterification reactor 18 through line 17 for the rectification column 5. The cited substances (referred to below as a whole as contaminants) are, i.a., ethylene glycol, acetic acid and acetaldehyde. They must be recovered for reasons of economy or removed to comply with environmental regulations. The process wastewater, that is the sum of (process) water and contaminants, is therefore subjected to one or more separation steps, wherein a first separation usually takes place by distillation in the rectification column 5. There most of the ethylene glycol present is separated, remaining in the sump, and which may then be either recovered or returned to the PET process (not shown in the drawing), and the overhead product of the column is subsequently fed to a condenser 6, wherein a part of the acetaldehyde and other low-boilers remain in the gas phase and are fed as exhaust air through line 9 to a thermal or catalytic combustion. Through a first separation step of this type a partially purified process wastewater is produced, which is optionally passed through a stripper 7 for separating out volatile components before it is fed into a water treatment plant comprising a cooler 11, a line 10 for channeling the partially purified waste water from the cooler to a prefilter 12, after which the partially purified waste water is passed to a reverse osmosis apparatus 13 comprising an osmotic membrane separating a chamber for the permeate and a chamber for the retentate. The permeate exits the process through line 15 where it is ready for final purification in a chemical-biological waste water treatment. Alternatively the partially purified waste water may be directly ejected from the process as wastewater. The retentate containing the partially purified waste water which still includes some MDO not already cleaved by hydrolysis exits the reverse osmosis apparatus through line 14 and is channeled to the collecting tank 1 where it is mixed with fresh SEG flow from line 2 from the various process steps of the PET process.

In addition to partially purified process wastewater, substantial quantities of contaminated ethylene glycol (spent ethylene glycol, SEG) accumulate in the PET production process, which contains, i.a., MDO. The SEG comes in particular through line 2 leading from the vacuum system 24 which communicates with the prepolycondensation reactor 21 through exhaust line 23. The SEG process flows from the various process steps of the PET production process are combined through line 2 in the collecting tank 1 (SEG tank or SEG collecting tank). There the MDO is contacted with the retentate from the osmosis channeled through line 14 and hydrolyzed at least in part, at an acid pH, preferably 3 to 6, and cleaved into ethylene glycol and acetaldehyde. The mixture comprising partially purified process wastewater and ethylene glycol recovered from MDO through hydrolytic cleavage is then led from the collecting tank through line 4 and subsequently subjected to a separation step in the rectification column 5, where the ethylene glycol flows to the sump of the rectification column and may then be returned to the PET production process (return not shown).

The MDO in the head of the rectification column is a low-boiler which cannot be held back in the rectification column, i.e., leaves the column overhead together with the (process) water. The large part of the MDO is then condensed together with the (process) water and discharged as part of the partially purified process wastewater, either to the stripper 7 or directly through line 16 to the water treatment plant. A small part of the MDO is emitted via the exhaust air 9.

The invention is described below based on examples, wherein the invention of course is not limited to these illustrated embodiments.

The illustrated embodiments show the composition of the material flows as they can occur in a system according to the invention for PET production with a capacity of 330 t/d. A process column is provided as the first separation step or as separation device for the process wastewater. Furthermore, an ethylene glycol enrichment by means of reverse osmosis takes place.

Abbreviations and Notes:

With respect to the designation of the material flows "Flow [no.]"), reference is made to the process diagram shown in FIG. 1.

The designation "*)" means that antimony acetate was used as a catalyst in the PET production process, whereas "**)" indicates the use of antimony trioxide as a catalyst in the PET production process.

LIST OF REFERENCE NUMBERS

1. Tank/SEG collecting tank
2. (Flow 2): SEG from prepolycondensation
3. (Flow 3): Exhaust air from container
4. (Flow 4): SEG+retentate from reverse osmosis
5. Process column
6. Condenser
7. Stripper system
8. (Flow 8): Air
9. (Flow 9): Total exhaust air for treatment
10. (Flow 10): Partially purified process wastewater after stripper
11. Cooler
12. Prefilter
13. Reverse osmosis unit
14. (Flow 14): Partially purified process wastewater/retentate from reverse osmosis
15. (Flow 15): Partially purified process wastewater/permeate from reverse osmosis 16. (Flow 16): Partially purified process wastewater after process column (alternative embodiment without the use of a stripper)
17. Line (for process wastewater in the form of process exhaust vapors)
18. Esterification reactor
19. Paste batch
20. Lines (for monomers)
21. (Pre)polycondensation reactor
22. Line (for polymer)
23. Line (for exhaust vapors from the (pre) polycondensation)
24. Vacuum device (including condenser)
25. Line (for exhaust air)

Example 1

The following tables show the material flows in a PET production process, wherein after running through a process column the process wastewater is subjected to another separation step (stripping with air):

Flow 10 (Partially Purified Process Wastewater after Stripper)

| Mass Flow (total) Water with: | 2400 kg/h |
|---|---|
| Ethylene glycol | 0.4% |
| 2-methyl-1,3 dioxolane | 0.03% |
| Acetic Acid | 0.15%*) |
| 1,4-dioxane | 0.03% |
| Acetaldehyde | Not relevant |
| Temperature | 35-45° C. |

Flow 14 (Partially Purified Process Wastewater: Retentate from Reverse Osmosis)

| Mass Flow (total) Water with: | 180 kg/h |
|---|---|
| Ethylene glycol | 4.3% |
| 2-methyl-1,3 dioxolane | 0.35% |
| Acetic Acid | 1%*) |
| 1,4-dioxane | 0.35% |
| Acetaldehyde | Not relevant |
| Temperature | 30-40° C. |

Retention Degrees of Reverse Osmosis:

| Ethylene glycol | 80% |
|---|---|
| 2-methyl-1,3 dioxolane | 85% |
| Acetic Acid | 50%*) |
| 1,4-dioxane | 90% |
| Acetaldehyde | Not relevant |

Flow 15 (Partially Purified Process Wastewater: Permeate from Reverse Osmosis)

| Mass Flow (total) Water with: | 2220 kg/h |
|---|---|
| Ethylene glycol | 0.1% |
| 2-methyl-1,3 dioxolane | 0.005% |
| Acetic Acid | 0.08%*) |
| 1,4-dioxane | 0.003% |
| Acetaldehyde | Not relevant |
| Temperature | 30-40° C. |

Discharge as wastewater for final purification in a chemical biological wastewater treatment.

Flow 2 (SEG from Prepolycondensation)

| Mass flow (total) Ethylene glycol with: | 1375 kg/h |
|---|---|
| Water | 5% |
| 2-methyl-1,3 dioxolane | 0.45% |
| Acetic Acid | 0.1%*) |
| 1,4-dioxane | 0.03% |
| Acetaldehyde | Not relevant |
| Temperature | 40° C. |

Conditions for MDO Cleavage in the SEG Collecting Tank (1)

| dwell time | 1.5 h |
|---|---|
| temperature | 45° C. |
| concentration of water | 15% |
| concentration of acid | 0.2% |
| exhaust air discharge suctioning off of the acetaldehyde formed, Discharge via exhaust air collector line to thermal or catalytic exhaust air treatment | |
| cleavage rate of MDO | 50% |

Flow 4 (SEG Flow+Retentate, after MDO Cleavage at 50%)

| Mass flow (total) Ethylene glycol with: | 1555 kg/h |
|---|---|
| Water | 15% |
| 2-methyl-1,3 dioxolane | 0.2% |
| Acetic Acid | 0.2%*) |
| 1,4-dioxane | 0.065% |
| Acetaldehyde | Not relevant |
| Temperature | 40° C. |

EG recovery rate - Free EG fed in addition to process column: 10.1 kg/h = 0.73 kg/t PET The acetaldehyde formed in addition to the ethylene glycol during the MDO cleavage is largely fed via the ventilation of the SEG collection tank via exhaust air collector line to a thermal or catalytic exhaust air purification.

Example 2

The following tables show the material flows in a PET production process, wherein in contrast to the method according to Example 1, the partially purified process wastewater is not stripped after running through the process column (5) and the condenser (6).

Flow 16 (Partially Purified Wastewater after Process Column and Condenser)

| | |
|---|---|
| Mass flow (total) | 2613 kg/h |
| Water with: | |
| Ethylene glycol | 0.5% |
| 2-methyl-1,3 dioxolane | 0.45% |
| Acetic Acid | 0.18%*) |
| 1,4-dioxane | 0.05% |
| Acetaldehyde | Not relevant |
| Temperature | 35-45° C. |

Flow 14 (Partially Purified Process Wastewater Retentate from Reverse Osmosis)

| | |
|---|---|
| Mass flow (total) | 180 kg/h |
| Water with: | |
| Ethylene glycol | 5.8% |
| 2-methyl-1,3 dioxolane | 5.5% |
| Acetic Acid | 1.3%*) |
| 1,4-dioxane | 0.65% |
| Acetaldehyde | Not relevant |
| Temperature | 30-40° C. |

Retention Degrees According to Reverse Osmosis

| | |
|---|---|
| Ethylene glycol | 80% |
| 2-methyl-1,3 dioxolane | 85% |
| Acetic Acid | 50% |
| 1,4-dioxane | 90% |
| Acetaldehyde | Not relevant |

Flow 15 (Partially Purified Process Wastewater: Permeate from Reverse Osmosis)

| | |
|---|---|
| Mass flow (total) | 2433 kg/h |
| Water with: | |
| Ethylene glycol | 0.1% |
| 2-methyl-1,3 dioxolane | 0.07% |
| Acetic Acid | 0.095%*) |
| 1,4-dioxane | 0.004% |
| Acetaldehyde | Not relevant |
| Temperature | 30-40° C. |

Discharge as wastewater for final purification in a chemical-biological wastewater treatment.

Flow 2 (SEG from Prepolycondensation)

| | |
|---|---|
| Mass flow (total) | 1375 kg/h |
| Ethylene glycol with: | |
| Water | 5% |
| 2-methyl-1,3 dioxolane | 0.45% |
| Acetic Acid | 0.1%*) |
| 1,4-dioxane | 0.03% |
| Acetaldehyde | Not relevant |
| Temperature | 40° C. |

Conditions for MDO Cleavage in the SEG Collecting Tank (1)

| | |
|---|---|
| dwell time | 1.5 h |
| temperature | 45° C. |
| concentration of water | 15% |
| concentration of acid | 0.2% |
| exhaust air discharge suctioning off of the acetaldehyde formed, Discharge via exhaust air collector line to thermal or catalytic exhaust air treatment | |
| cleavage rate of MDO | 50% |

Flow 4 (SEG Flow+Retentate, after MDO Cleavage at 50%)

| | |
|---|---|
| Mass flow (total) | 1555 kg/h |
| Ethylene glycol with: | |
| Water | 14% |
| 2-methyl-1,3 dioxolane | 0.5% |
| Acetic Acid | 0.24%*) |
| 1,4-dioxane | 0.1% |
| Acetaldehyde | Not relevant |
| Temperature | 40° C. |

EG recovery rate: Free EG fed in addition to process column 16.2 kg/h = approx. 1.2 kg/t PET The acetaldehyde formed in addition to the ethylene glycol during the MDO cleavage is largely fed via the ventilation of the SEG collecting tank via exhaust air collector line to a thermal or catalytic exhaust air purification.

What is claimed is:

1. A process for recovering ethylene glycol from 2-methyl-1,3-dioxolane (MDO), in which ethylene glycol is bonded in the form of an acetal, during production of polyethylene terephthalate from ethylene glycol and terephthalic acid, which comprises the steps of:
    (a) subjecting ethylene glycol and terephthalic acid to an esterification reaction to form ethylene terephthalate and a process waste water containing contaminants, which include ethylene glycol, separating the ethylene terephthalate from the process waste water and subjecting the ethylene terephthalate to a polycondensation reaction to form polyethylene terephthalate;
    (b) subjecting the process waste water obtained from step (a), to at least one separation step in a rectification column, in which the contaminants present in the process waste water, including ethylene glycol, are partially separated from the process waste water, to collect in the sump of the rectification column, and to obtain as a head product a partially purified process waste water; and
    (c) mixing in a collecting tank at least a part of the partially purified process waste water obtained according to step (b) with a fluid containing 2-methyl-1,3-dioxolane (MDO), said fluid obtained from one or more ethylene glycol process flows, upstream of the rectification column, and as a result of an increase in the water content in the fluid, a shift in the reaction equilibrium takes place and consequently a hydrolytic cleavage of the 2-methyl-1,3-dioxolane takes place so that at least a portion of the 2-methyl-1,3-dioxolane (MDO) is hydrolytically cleaved into ethylene glycol and acetaldehyde, before passing the mixture into the rectification column according to step (b).

2. The process defined in claim 1 wherein following step (b), at least a part of the partially purified process wastewater is subjected to a reverse osmosis and/or ultra/nanofiltration before the mixing with the fluid containing 2-methyl-1,3-dioxolane (MDO) according to step (c), wherein that part of the partially purified process wastewater which accumulates following the reverse osmosis and/or ultra/nanofiltration as retentate is used at least in part for mixing with the fluid containing 2-methyl-1,3-dioxolane (MDO) according to step (c), and wherein that part of the partially purified process waste water which does not accumulate, is recovered as a permeate from the reverse osmosis, which is discharged for final purification in a chemical-biological waste water treatment.

3. The process defined in claim 2, wherein according to step (c) the cleavage of the MDO into ethylene glycol and acetaldehyde is carried out in the presence of at least one catalyst.

4. The process defined in claim 3, wherein the catalyst is at least one aliphatic or aromatic carboxylic acid.

5. The process defined in claim 4, wherein the catalyst is acetic acid.

6. The process defined in claim 4, wherein the at least a part of the partially purified process wastewater subjected to a reverse osmosis yields a retentate which contains reconcentrated aliphatic or aromatic carboxylic acid catalyst used to catalyze the cleavage of 2-methyl-1,3-dioxolane (MDO) according to step (c).

7. The process defined in claim 1, wherein the mixture obtained according to step (c) has a water content of at least 10% by weight.

8. The process defined in claim 7, wherein the mixture obtained according to step (c) has a water content of 13 to 45% by weight.

9. The process defined in claim 8, wherein the mixture obtained according to step (c) has a water content of 15 to 25% by weight.

10. The process defined in claim 2, wherein the retentate, which is recovered following the reverse osmosis includes at least part of any 1,4-dioxane contaminant, present in the partially purified process waste water.

* * * * *